United States Patent [19]
Adler et al.

[11] 3,964,434
[45] June 22, 1976

[54] COATING APPARATUS INCLUDING LIQUID SEALANT BETWEEN COMPARTMENTS

[75] Inventors: Stanford L. Adler, Monsey; Alexander M. Saunders, Bedford Village, both of N.Y.

[73] Assignee: Technicon Instruments Corporation, Tarrytown, N.Y.

[22] Filed: Nov. 4, 1974

[21] Appl. No.: 520,586

[52] U.S. Cl. ............................ 118/405; 118/506
[51] Int. Cl.² .......................................... B05C 3/15
[58] Field of Search .................. 118/49.1, 49.5, 405, 118/419, 429, 42, 420; 427/434, 2; 34/242; 134/64, 75, 77, 114

[56] References Cited
UNITED STATES PATENTS

| | | | |
|---|---|---|---|
| 1,614,562 | 1/1927 | Laise | 118/420 X |
| 2,384,500 | 9/1945 | Stoll | 118/49 X |
| 2,458,394 | 1/1949 | Lubosnez | 118/419 |
| 2,679,823 | 6/1954 | Denham | 118/405 |
| 3,326,177 | 6/1967 | Taylor | 118/49.1 |
| 3,516,345 | 6/1970 | Meyer | 118/405 |
| 3,549,424 | 12/1970 | Rice | 118/49.1 X |
| 3,647,530 | 3/1972 | Dyer | 118/49.5 X |
| 3,658,680 | 4/1972 | Combe et al. | 118/49.1 X |
| 3,683,846 | 2/1972 | Flournoy et al. | 118/49.5 |
| 3,854,440 | 12/1974 | Astle | 118/429 |

Primary Examiner—Morris Kaplan
Attorney, Agent, or Firm—S. P. Tedesco; Stephen E. Rockwell

[57] ABSTRACT

Apparatus is described for treating substances carried or affixed to a surface of a continuous substrate, e.g., a ribbon or tape, with successive treating fluids including liquids contained in a series of treating chambers, adjacent chambers being separated by a high surface tension liquid, e.g., mercury. The chambers may be defined by hollow walls having slots located below the level of the treating fluids in the adjacent treating chambers, such slots being dimensioned to allow passage of the tape between the adjacent treating chambers and to prevent dislocation of the high-surface tension liquid, which is located in the hollow walls and serves to wipe excess treating fluid from the tape during passage between the adjacent treating chambers, so as to prevent carryover therebetween.

7 Claims, 8 Drawing Figures

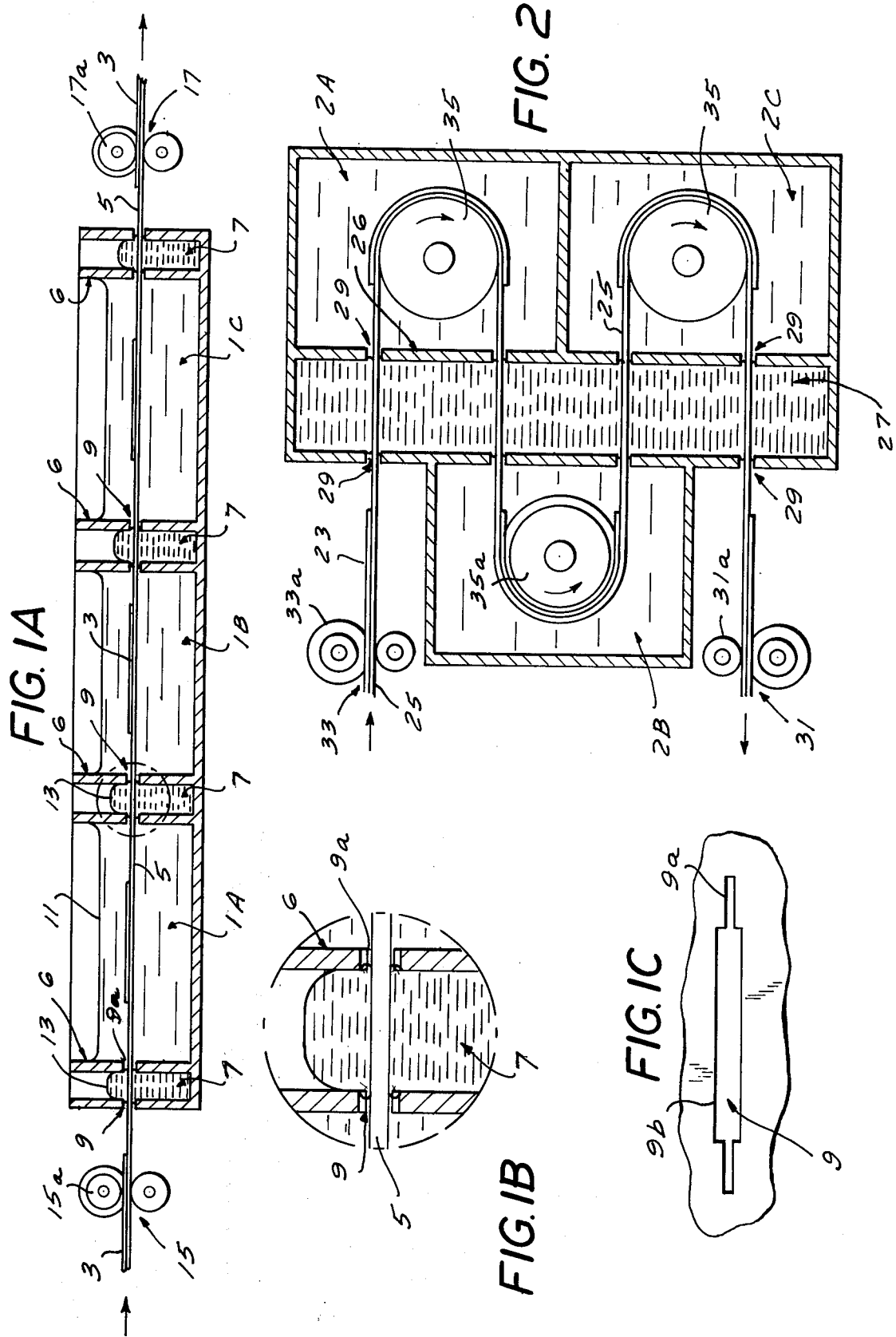

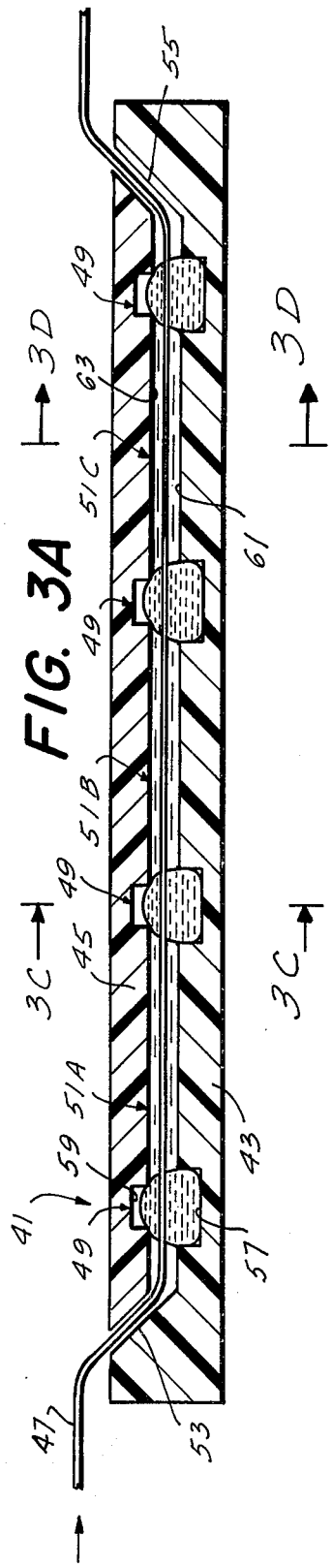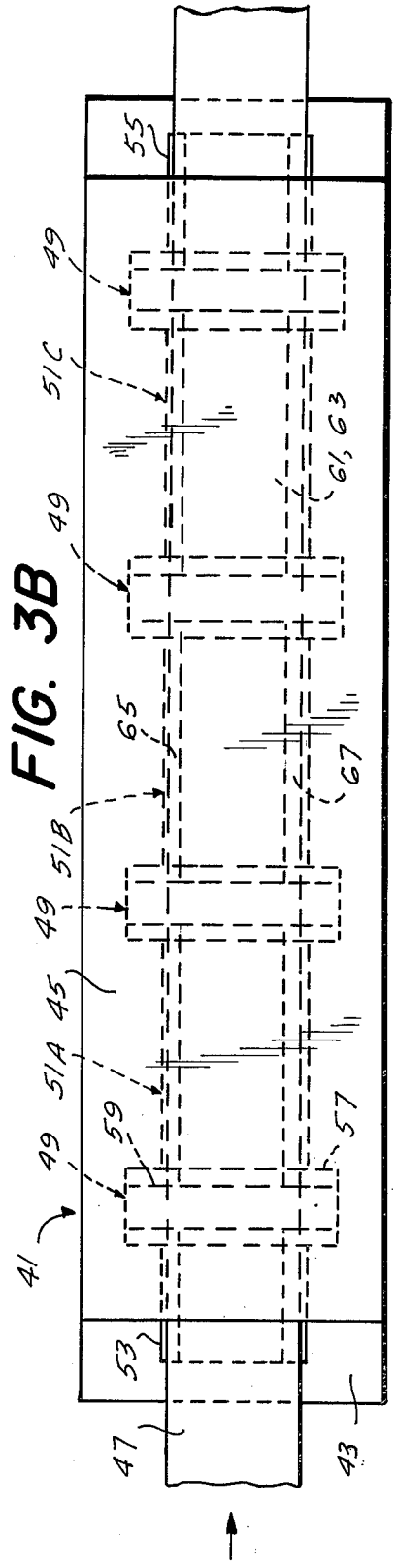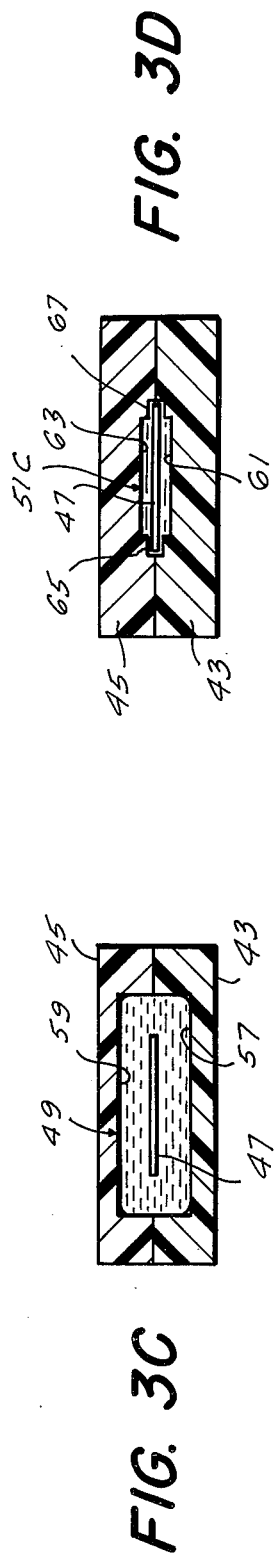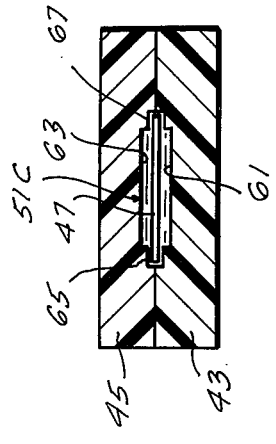

COATING APPARATUS INCLUDING LIQUID SEALANT BETWEEN COMPARTMENTS

BACKGROUND OF THE INVENTION

1. Field of the Invention

The present invention relates to apparatus for successively treating a substance carried upon or affixed to a surface of a continuous ribbon or tape with different treating liquids, by advancing such tape through a series of such liquids, and finds particular application in the treatment for microscopic examination of biological smears deposited on a tape, as described in U.S. Ser. No. 375,223, now U.S. Pat. No. 3,861,197, assigned to the assignee of the present invention. However, the invention finds broad application in those cases where substances carried upon or affixed to a continuous surface or sequential surface areas are to be successively treated by a plurality of liquids.

2. Prior Art

Heretofore, biological substances have been prepared for microscopic examination by applying or smearing the same onto glass microscopic slides, by known techniques. Subsequently, these biological smears were subjected to various procedures, according to the particular effect desired, to stain the various cells and facilitate differentiation of different cell types while examined under a microscope by an examiner. Such staining procedure required that the smear be treated by exposing the same to various liquids including dyes, e.g., thiazine dyes, oxazine dyes, etc. Such procedure, when done manually, necessitated that the smear be exposed to air between successive dippings and washings in the various liquid reactants by the operator. Conventionally, a microscopic slide, with the smear affixed to one surface, is dipped successively into a plurality of liquid reactants for predetermined time intervals and then washed. Depending upon the particular staining procedure, as many as ten or twelve liquid reactants might be required. Such manually performed prior art treatment of biological smears was time consuming. Also, there was considerable danger of carryover between the liquid reactants by the microscopic slides and frequent recycling of the liquid reactants was necessary.

In U.S. Pat. No. 3,431,886, there is shown an apparatus for the automatic staining of microscopic slides, by effectively contacting the biological smear carried thereon with a plurality of liquid reactants, in turn. Such apparatus operates to move the slide through a number of treatment stations, whereat the surface of the slides carrying the biological smear is exposed to a metered quantity of unused reactants.

In U.S. Ser. No. 375,223, an apparatus is particularly disclosed for depositing biological smears onto a ribbon or tape, which is not particularly susceptible to treatment by conventional prior art techniques. The present invention finds particular application in the treatment of such biological smears disposed successively.

SUMMARY OF THE INVENTION

A primary object of the present invention is to provide an apparatus for the automated processing of substances carried upon or affixed to a continuous surface of a superstrate or substrate sequentially by a plurality of fluids including reactants. For example, in the processing of a tape containing biological smears which have been successively deposited thereon, as per the apparatus disclosed in U.S. Ser. No. 375,223, one or more primary or treating chambers are arranged tandemly, each containing an appropriate liquid reactant. The treating chambers may be formed in adjacent and sequential fashion, adjacent chambers being separated by a hollow-wall, which constitutes a secondary or isolation chamber. Each isolation chamber has in-line opposing openings, or slots, disposed below the level of the liquid reagents in the adjacent treating chambers and is filled with a liquid having a high-surface-tension characteristic. The slots in the isolation chambers may be aligned in a single plane, as to allow passage of the tape through each of the treating chambers in straight-line fashion. The high-surface-tension liquid is mercury, for example. The characteristics of the high-surface-tension liquid are such as to prevent diffusion of liquid reactants between the adjacent treating chambers and, advantageously, to prevent carryover therebetween by the tape. Because of its density and non-wetting action, such liquid acts to wipe excess liquids and precipitates from the tape. Also, the slits are disposed below the level of the liquid reactants in the adjacent treating chambers, such that the ribbon tape is introduced into each chamber below the level of the reactant fluid therein. Such feature avoids passage of the tape through the surface of the reactants, whereat precipitates formed by the treatment of biological smears tend to accumulate.

BRIEF DESCRIPTION OF THE DRAWINGS

In the drawings:

FIG. 1A is a cross-sectional view of a preferred embodiment of the present invention;

FIG. 1B is an enlarged cross-sectional view of the opposing slots in the secondary or isolation chamber of the embodiment of FIG. 1A;

FIG. 1C is a frontal view particularly illustrating the geometry of the opposing slots in the secondary or isolation chambers of FIG. 1A.

FIG. 2 is a top view of an alternate embodiment of the present invention;

FIG. 3A is a longitudinal elevational view in section illustrating a further modification of the invention;

FIG. 3B is a top plan view of the modification of FIG. 3

FIG. 3C is an enlarged sectional view taken on line 3C—3C of FIG. 3A; and

FIG. 3D is a view similar to FIG. 3C taken on line 3D—3D of FIG. 3A.

DESCRIPTION OF THE PREFERRED EMBODIMENT

Referring to FIG. 1, an apparatus according to the present invention comprises a plurality of primary treating chambers 1A, 1B and 1C, each containing an appropriate liquid for selectively treating biological samples such as tissue sections or smears 3 which have been deposited onto the surface of a ribbon tape 5. Biological smears 3 may comprise, for example, blood smears formed on tape 5 by the apparatus described in the copending U.S. Ser. No. 375,223. The number of treating chambers would be equal to the number of liquid reactants required for treatment of the biological smears 3 and any wash solution. For example, to effect treatment of a blood smear by the wellknown Romanowsky technique, treating chambers 1A–1C could contain, typically, a saturated alcoholic stain (methyline blue and eosine), a buffer solution (Phosphate buffer in the pH range of 6.4 to 6.8), and a wash solution (distilled water), respectively.

Treating chambers 1A–1C are arranged in tandem and each is defined by a pair of opposite hollow walls, indicated generally at 6, of narrow dimensions, each of which defines a secondary or isolation chamber 7. A pair of oppositely disposed slots 9 are formed in the hollow walls of each isolation chamber 7, so as to allow passage therethrough of tape 5. As illustrated, slots 9 in each of the isolation chamber 7 are disposed in a single plane, so as to allow passage of tape 5 in straight-line fashion therethrough and through each of the treatment chambers 1A–1C. particularly in FIGS. 1B and 1C, the dimensions of the extreme portions 9a of each slot 9 are reduced to provide positive guidance therethrough of tape 5. The central portion 9b of each slot 9 is of sufficient dimension to accommodate and allow clear passage therethrough of a biological sample smear 3 supported on tape 5.

Each of the treating chambers 1A–1C and isolation chambers 7, formed by respective containers, is filled with an appropriate liquid to a level, at least, above that of slots 9. In other words, the liquid level 11 in treating chambers 1A–1C and the liquid level 13 in isolation chambers 7 is above the tape 5 which is passed through slots 9. As indicated, isolation chambers 7 are each filled to a level above that of slots 9 with a liquid having high-surface-tension characteristics and which is immiscible and inert with respect to the liquid reagents. Also, such liquid should be inert with respect to tape 5 and the biological sample smears 3. Liquids suitable for such purposes are mercury and alloys of gallium which are liquid at the operating temperatures of the invention, e.g., room temperature. Accordingly, tape 5 is not passed through the top surface of any of the liquids contained in either treating chambers 1A–1C or isolating chambers 8, during treatment.

Tape 5 is moved in the direction of the arrow by guide roller arrangement 15 and drive roller arrangement 17. The upper rollers 15a and 17a of such arrangements are stepped to have central portion recesses to provide clearance so as to avoid compressing the biological samples 3 on tape 5. As tape 5 is passed through the first isolation chamber 7 formed by a container and the liquid contained therein, e.g., mercury, it closely confines the tape surfaces without damage to the biological sample smear 3. In addition, the mercury is retained within the first isolation chamber 7, so as to provide an effective seal and prevent loss of the liquid reactant.

To continue the example, Tape 5 is introduced into the first treating chamber 1A and treated by the alcoholic stain, which fixes the cells in the biological smear and selectively stains the basophilic structures in the cells. The longitudinal dimension of treating chamber 1A is such that the dwell time, as a function of the rate or periodicity of advance of Tape 5, is sufficient to properly treat the biological smear. Because of the high-surface-tension and non-wetting characteristics of the mercury, the biological sample smear 3 is totally undamaged. Also, it should be appreciated that tape 5 is introduced below the level 11 of the liquid reagent contained in treating chamber 1A. Accordingly, any solids or by-products formed during treatment of a biological sample smear 3 tend to float or precipitate, depending upon their relative specific gravities, away from the surface of tape 5 in the liquid reactant. Since tape 5 is not passed through the surface of the liquid reagent, the possibility of such by-products contaminating or becoming affixed to such tape is avoided. This is a major advantage over art techniques, wherein microscopic slides or equivalents thereof supporting biological smears are immersed and withdrawn from the reactant bath through the liquid surface, whereat by-products of the treatment have accumulated. Such prior art techniques, therefore, exposes such microscopic slides to contamination. Also, any significant accumulation of these by-products on the liquid surface would require frequent replacement of the liquid reactant.

Tape 5, treated by the liquid reagent in treating chamber 1A, is passed through the slots 9 defined in the second isolation chamber 7 and into the second treating chamber 1B formed by a container. In passing through slots 9 of the second isolation chamber 7, the mercury tends to strip excess treating liquid from tape 5, to avoid carryover between the first and second treating chambers 1A and 1B. Also, any foreign material carried by tape 5 tends to be dislodged and removed from the surface of the tape.

Tape 5 is passed into treating chamber 1B. whereat the biological sample smears 3 are appropriately treated for example with the buffer solution contained therein, such as to dilute the alcoholic stain carried by the cells and complete the balance of the staining process under appropriate pH conditions, as commonly practiced in the art. Also, the longitudinal dimension of treating chamber 1B or periodicity of tape advance is determined to provide a sufficient dwell time within such chamber to effect proper treatment of the biological smear 3. As before, any by-products formed during this treatment float or precipitate away from the path of tape 5. Accordingly, tape 5 is exposed only to the interior volume of the liquid reagent contained in each treating chamber.

The same procedure is repeated in passing tape 5 through any number of successive treating or wash chambers, the interposed isolation chamber 7 acting to prevent carryover therebetween. In both the treating and isolation chambers, tape 5 is exposed only to clean "liquid" and is not exposed, during treatment, to the ambient, which would contain airborn dust and vapors which could affect the smear. The final treating chamber 1C, preferably, contains an appropriate wash solution: alternatively, such chamber can define a sealed drying chamber for drying tape 5 before exposure to the ambient. Tape 5 passing from the final treating chamber 1C can be directed through the final isolation chamber 7 formed by a container to a microscopic viewing station, whereby each fully treated biological smear is passed through the viewing plane of a microscope, in turn, for examination or, alternately, can be severed or spooled-up for storage and subsequent examination of the individual biological smears 3.

An alternate embodiment of the invention is shown in FIG. 2, which illustrates an arrangement wherein a plurality of treating chambers 2A, 2B and 2C are disposed in staggered parallel rows, the rows being separated by a single hollow wall, indicated generally at 26, defining isolation chamber 27, as shown. Isolation chamber 27 is provided with a plurality of opposing slots 29, dimensioned as shown in FIG. 1B, to allow introduction and withdrawal of tape 25 supporting a number of biological sample smears 23 with reference to the treating chambers 2A, 2B and 2C. containing the liquids described above, for treating the smears according to the Romanowsky procedure. The liquid levels in each of the treating chambers 2A, 2B, and 2C and in isolation chamber 27 are above the path of movement of tape 25, as described with respect to FIG. 1A.

Drive roller arrangement 31 and guide roller arrangement 33 are provided to pass tape 25 through each of treating chambers 2A, 2B and 2C, rollers 31a and 33a being stepped to accommodate the biological smears, as previously described. Each treating chamber includes a roller 35, so as to direct the tape 25 in serpentine fashion through each of the treatment chambers, in turn. To prevent damage to the biological smears carried by tape 25, the idle roller 35a is stepped, with the central portion recessed, to accommodate the biological smears 23.

Again, the liquid in the common isolation chamber 27 serves the dual function of sealing each of the treating chambers 2A, 2B and 2C and stripping excess treating liquid from tape 25 to prevent carryover therebetween. Again, since tape 25 is passed below the surface levels of the liquids in treating chambers 2A–2C and the liquid in isolation chamber 27, it is exposed only to "clean" liquids, the replacement frequency of the liquid reactants is reduced.

It will be understood from the foregoing that the device which forms the chambers 1A–1C and 7 is a unitary device similar to the device of FIG. 2 which forms the chambers 2A–2C and the chamber 27. However, particularly with reference to the aforementioned device of FIG. 1A, it will be clearly understood that this device need not be formed as a unitary structure. By this it is meant that the means defining chambers 1A–1C may be a series of containers and the means, namely the hollow wall structures 6 may be formed as separate containers. The only requirement is that the containers either have the illustrated common wall structures 6 or that, if such common wall structures do not exist, the chambers abut one another in sealing relationship and are provided with slots 9 therethrough. Further, while reference has been made to treatment of one or more surfaces of a continuous ribbon or tape it will be evident, particularly with reference to FIG. 1A, that the surfaces treated may be those on successive glass slides, each supporting a biological specimen, passed in contiguous fashion, as by pushing of the slides along the guides 9 aof FIG. 1C. Still further, the treating chambers may be sealed or covered such that the reactant fluid may be a gaseous or radiant energy. In the latter case, the covering should be such as to exclude ambient light which might deleteriously affect the treatment. Moreover, it is to be noted that the material from which the reaction chambers 1A–1C are formed should be an appropriate inert material.

In the modified form FIGS. 3A–3D there is shown a support similar to the support which provides the chambers 1A–1C for the form of FIG. 1, which support may take the form of a shallow receptacle, indicated generally at 41, of box-like form having a bottom 43 and a lift-off cover 45. The cover 45 may be supported from the bottom 43, as shown in FIGS. 3C and 3D. The receptacle 41 defines between the bottom 43 and top 45 thereof a passageway therethrough for a tape 47, such as the previously described tape 5, which may be structured of an inert plastic material such as Mylar carrying thereon at spaced intervals biological smears to be treated in the manner described with reference to the form FIG. 1A. The tape itself may have a thickness of 0.004 inch by way of example.

The receptacle 41 has in the coacting bottom 43 and top 45 fluid treatment chambers 51A–51C separated one from another by isolation chambers 49 defined by the bottom and top. It will be noted that such isolation chambers 49 are also located at the entrance to chamber 51A and at the exit of chamber 51C, and that the isolation chambers 49 are of larger vertical dimension (FIG. 3C) such as 0.015 inch, by way of example and not by way of limitation. As indicated in FIG. 3A and FIG. 3D, the chambers 51A–51C are shallower than the chambers 49, one of which is shown in FIG. 3C.

The receptacle bottom 43 and top 45 define therebetween a tape inlet 53 and a tape outlet 55, with a tape 47 moving in the direction of the arrow of FIG. 3A. The tape may be advanced periodically by any suitable drive mechanism such as the aforementioned roller drive assembly of FIG. 1A to provide the proper dwell time of each biological smear in each of the treatment chambers 51A–51C. The cross section of one of the chambers 49 is shown in FIG. 3C and is dimensionally larger in all directions than the chambers 51A–51C. An upper surface portion 57 of the bottom 43 provides the lower extremity of the chamber 49, the corresponding upper extremity being indicated at 59. The last-mentioned surface is defined by an undersurface portion of the top 45 of the receptacle.

It should be noted that the tape 47 is completely unconfined by the structure of the receptacle 41 in the area of each chamber 49. The lower extremities of the isolation chambers 49, one being shown, as previously indicated, at 57 in FIG. 3C, are located below the lower extremities of the treatment chambers, one such lower extremity being indicated at 61 in FIG. 3D. The chambers 49 are formed in part as notches in the upper surface of the bottom 43 and opposing notches in the undersurface of the top 45. As indicated in FIG. 3B, the notches are of a length exceeding the cross-sectional dimension of the tape 47 and the cross section of the chambers 51A–51C. However, as clearly shown in FIGS. 3A, the wall structure defining these notches in the bottom 43 and top 45 do not meet.

The chambers 49 defined by the aforesaid notches are filled to a height above the fluid level in the treatment chambers 51A–51C with a non-wetting, high density, immiscible liquid having high-surface-tension characteristics, e.g., mercury. For example, on such filling, with the cover 45 removed, the lower portions of the isolation chambers 49 formed by the bottom 43 are filled to the last-mentioned height with mercury. The chambers 51A–51C are thereafter filled with the reactant fluid to a level below the meniscus of each volume of mercury, such that the volumes of mercury separate and isolate such treatment fluids. When the cover is in place, the meniscus of each volume of mercury extends into the corresponding notch formed in part by the surface portion 59 of the undersurface of the top 45 in a manner such that the meniscus of the mercury has a sealing effect against the vertical wall portions of such notch.

The chambers 51A–51C are substantially filled with the treating fluids, one of which may be a wash solution as in the form FIG. 1A. The tape may be threaded through the aforementioned passageway of the receptacle utilizing the lateral extensions, a pair being shown at 65 in FIG. 3D, which extensions form tape guides. It is to be noted that in FIG. 3A the wetting angle of the meniscus of mercury has not been shown with any degree of accuracy but has been shown solely for the purpose of the illustration of the invention which will be understood from the foregoing description.

As clearly brought out in the foregoing description of the modification of FIGS. 3A–3D, there are no walls as such between the isolation chambers 49 and the treatment chambers 51A–51C, hence, there are no slots such as the slots 9 in the structure defining the hollow walls 6 of FIG. 1A or the hollow wall 26 of FIG. 2. In the form of FIG. 3A, isolation liquid, e.g., mercury is retained in its respective locations by the characteristics of the liquid previously defined. As the tape moves through the device of FIG. 3A, through the treatment fluids and the isolation liquid, for treatment of biological smears thereon, the volumes of the isolation liquid serve exactly the same functions as the volumes of the isolation liquid in the operation of the device of FIG. 1A previously described.

While several forms of the invention have been illustrated and described, it will be apparent, especially to those versed in the art, that the invention may take other forms and is susceptible to various changes in details without departure from the principles of the invention.

What is claimed is:

1. Apparatus for treating a continuous surface of a web with different fluids including reactants comprising:

at least a pair of treating chambers having a common wall therebetween and an entry and an exit slot disposed in respective side walls lying in the same general plane;

a sealing chamber defined in part by said side walls;

at least a third treating chamber having in common with said sealing chamber a wall opposed to said side walls;

a first pair of slots in said opposed wall, each of said last mentioned slots being alined with one of said entry or exit slots of a separate prior recited treating chamber;

a second pair of slots in said opposed wall which are external to said third treating chamber and each of said last mentioned slots being alined with a separate one of the other of said entry or exit slots;

a treating fluid in each of said treating chambers at a level above said slots associated therewith;

a liquid sealant disposed in said sealing chamber to a level above each of said slots, having a high-surface-tension characteristic and being immersible and inert with respect to each of said treating fluids;

each of said slots being of a dimension whereby to retain said sealant by surface tension; and roller guide means operatively associated with each of said chambers whereby said web may enter and exit from said apparatus through said sealing chamber and travel sequentially through each of the alined pairs of slots for treatment in each of the three recited treating fluids.

2. Apparatus as defined in claim 1 wherein: said liquid is mercury.

3. Apparatus as defined in claim 1 wherein: said liquid is an alloy of gallium.

4. Apparatus as defined in claim 1, wherein: said continuous surface of said web has deposited thereon biological samples at spaced intervals therealong, at least certain of said treating fluids being effective to react with said samples.

5. Apparatus as defined in claim 1, wherein: said web is a flexible tape.

6. Apparatus as defined in claim 1 wherein: the end portions of each said slot is are of a reduced dimension.

7. Apparatus as defined in claim 1, wherein: said reactants are of liquid form and are selected from a group consisting of thiazine dyes and oxazine dyes.

* * * * *